(12) United States Patent
Osadchy et al.

(10) Patent No.: US 10,398,348 B2
(45) Date of Patent: Sep. 3, 2019

(54) BASELINE IMPEDANCE MAPS FOR TISSUE PROXIMITY INDICATIONS

(71) Applicant: BIOSENSE WEBSTER (ISRAEL) LTD., Yokneam (IL)

(72) Inventors: Daniel Osadchy, Haifa (IL); Meir Bar-Tal, Haifa (IL); Liron Shmuel Mizrahi, Kiryat Bialik (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 133 days.

(21) Appl. No.: 15/788,286

(22) Filed: Oct. 19, 2017

(65) Prior Publication Data

US 2019/0117111 A1    Apr. 25, 2019

(51) Int. Cl.
| | |
|---|---|
| *A61B 5/00* | (2006.01) |
| *A61B 5/06* | (2006.01) |
| *A61B 5/042* | (2006.01) |
| *A61B 5/04* | (2006.01) |
| *A61M 25/01* | (2006.01) |

(52) U.S. Cl.
CPC .............. *A61B 5/063* (2013.01); *A61B 5/042* (2013.01); *A61B 5/04012* (2013.01); *A61B 5/6858* (2013.01); *A61B 2562/0209* (2013.01); *A61M 2025/0166* (2013.01)

(58) Field of Classification Search
CPC ....... A61B 5/063; A61B 5/061; A61B 5/6858; A61B 5/6859; A61B 5/0538
See application file for complete search history.

(56) References Cited

U.S. PATENT DOCUMENTS

| | | |
|---|---|---|
| 8,456,182 B2 | 6/2013 | Bar-Tal et al. |
| 2009/0163904 A1 | 6/2009 | Miller et al. |
| 2010/0286550 A1 | 11/2010 | Harlev et al. |
| 2012/0184863 A1 | 7/2012 | Harlev et al. |
| 2014/0095105 A1 | 4/2014 | Koyrakh et al. |
| 2016/0143686 A1 | 5/2016 | Tunay et al. |
| 2016/0242667 A1 | 8/2016 | Fay et al. |

FOREIGN PATENT DOCUMENTS

WO    WO 2016/181316    11/2016

OTHER PUBLICATIONS

European Search Report dated Feb. 26, 2019 from corresponding European Patent Application No. 18201142.9.

*Primary Examiner* — Scott M. Getzow
(74) *Attorney, Agent, or Firm* — Vincent J. Serrao (57) ABSTRACT

A processor is configured to construct a baseline impedance model (BIM) that models a portion of a heart of a subject as a collection of three-dimensional cells, each of which corresponds to a respective volume within the heart, at least some of the cells being designated as baseline-impedance cells, for each of which the BIM specifies a respective baseline impedance, to ascertain, based on a signal received via an electrical interface, an impedance between a catheter electrode, which is within the heart, and an external electrode that is externally coupled to the subject, to identify one of the baseline-impedance cells as a reference cell, to ascertain that the catheter electrode is within a threshold distance of tissue of the heart, by comparing the ascertained impedance to the baseline impedance that is specified for the reference cell, and to update a map of the tissue in response to the ascertaining.

36 Claims, 5 Drawing Sheets

BASELINE IMPEDANCE MAPS FOR TISSUE PROXIMITY INDICATIONS

FIELD OF THE INVENTION

The present invention relates to the field of medical devices, and particularly to intracardiac catheters, such as catheters for electroanatomical mapping.

BACKGROUND

In some applications, a catheter, comprising one or more electrodes, is inserted into the heart of a subject, and is subsequently used to perform an electroanatomical mapping of the tissue of the heart, and/or to perform another function.

US Patent Application Publication 2010/0286550, whose disclosure is incorporated herein by reference, describes a method that includes inserting a catheter into a heart, the catheter comprising three or more electrodes, causing current to flow between at least some of the electrodes, and in response to current flow, measuring an electrical signal at each of one or more of the electrodes. The method further includes determining a boundary of at least a portion of the heart based on the measured electrical signals, and displaying a portion of less than the entire boundary of the heart.

SUMMARY OF THE INVENTION

There is provided, in accordance with some embodiments of the present invention, an apparatus that includes an electrical interface and a processor. The processor is configured to construct a baseline impedance model (BIM) that models a portion of a heart of a subject as a collection of three-dimensional cells, each of which corresponds to a respective volume within the heart, at least some of the cells being designated as baseline-impedance cells, for each of which the BIM specifies a respective baseline impedance. The processor is further configured to ascertain, based on a signal received via the electrical interface, an impedance between a catheter electrode, which is within the heart, and an external electrode that is externally coupled to the subject. The processor is further configured to identify one of the baseline-impedance cells as a reference cell, to ascertain that the catheter electrode is within a threshold distance of tissue of the heart, by comparing the ascertained impedance to the baseline impedance that is specified for the reference cell, and to update a map of the tissue, in response to ascertaining that the catheter electrode is within the threshold distance of the tissue.

In some embodiments, the processor is configured to update the map of the tissue to incorporate a location of the catheter electrode, in response to ascertaining that the catheter electrode is within the threshold distance of the tissue.

In some embodiments, the processor is configured to update the map of the tissue to incorporate information contained in an electrocardiographic signal acquired by the electrode, in response to ascertaining that the catheter electrode is within the threshold distance of the tissue.

In some embodiments, the processor is configured to identify the one of the baseline-impedance cells as the reference cell in response to a center of the one of the baseline-impedance cells corresponding to a location that is closer to a location of the catheter electrode than is any other location to which a center of any other one of the baseline-impedance cells corresponds.

In some embodiments, the processor is configured to identify the one of the baseline-impedance cells as the reference cell in response to a location of the catheter electrode being included in the volume to which the one of the baseline-impedance cells corresponds.

In some embodiments, the processor is configured to compare the ascertained impedance to the baseline impedance that is specified for the reference cell by:

computing a ratio between a real component of the ascertained impedance and a real component of the baseline impedance, and comparing the ratio to a ratio threshold.

In some embodiments, the processor is configured to compare the ascertained impedance to the baseline impedance that is specified for the reference cell by:

computing a difference between a phase of the ascertained impedance and a phase of the baseline impedance, and comparing the difference to a phase-difference threshold.

There is further provided, in accordance with some embodiments of the present invention, an apparatus that includes an electrical interface and a processor. The processor is configured to ascertain, for each volume of a plurality of different volumes within a heart of a subject, one or more impedances between a catheter electrode, which is in the volume, and an external electrode that is externally coupled to the subject, based on a signal received via the electrical interface. The processor is further configured to construct a baseline impedance model (BIM) that models a portion of the heart as a collection of three-dimensional cells, each of which corresponds to a respective one of the volumes, by, for each cell of a first subset of the cells, calculating a respective representative impedance, based on the one or more impedances ascertained for the volume to which the cell corresponds, and designating a second subset of the cells, which is a subset of the first subset of the cells, as baseline-impedance cells, each cell of which has, as a respective baseline impedance, the representative impedance of the cell. The processor is further configured to ascertain, subsequently to constructing the BIM, that the catheter electrode is within a threshold distance of tissue of the heart, based on the baseline impedance of one of the baseline-impedance cells, and to update a map of the tissue, in response to ascertaining that the catheter electrode is within the threshold distance.

In some embodiments, the processor is configured to calculate the representative impedance of the cell by averaging at least some of the impedances ascertained for the volume to which the cell corresponds.

In some embodiments, the threshold distance is a first threshold distance, and the processor is configured to designate the second subset of the cells as the baseline-impedance cells by, for at least one cell of the second subset:

identifying, as a third subset of the cells, other cells of the first subset that are within a second threshold distance from the cell, designating the cell as a potential baseline-impedance cell, based on respective representative impedances of the third subset of the cells, subsequently to designating the cell as a potential baseline-impedance cell, identifying, as a fourth subset of the cells, other cells of the first subset that are also designated as potential baseline-impedance cells, and are within a third threshold distance from the cell, and designating the cell as one of the baseline-impedance cells, based on respective representative impedances of the fourth subset of the cells.

In some embodiments, the processor is configured to designate the cell as a potential baseline-impedance cell by:

calculating at least one measure of similarity between the representative impedance of the cell and the respective representative impedances of the third subset of the cells, calculating at least one measure of variation of the respective representative impedances of the third subset of the cells, and designating the cell as a potential baseline-impedance cell in response to the measure of similarity and the measure of variation.

In some embodiments, the processor is configured to designate the cell as one of the baseline-impedance cells by:

calculating at least one measure of similarity between the representative impedance of the cell and the respective representative impedances of the fourth subset of the cells, and designating the cell as one of the baseline-impedance cells in response to the measure of similarity.

In some embodiments, the processor is configured to designate the cell as one of the baseline-impedance cells by:

fitting a line to the respective representative impedances of the fourth subset of the cells, and designating the cell as one of the baseline-impedance cells, in response to a distance between the representative impedance of the cell and the line being less than a fourth threshold distance.

In some embodiments, the threshold distance is a first threshold distance, and the processor is configured to designate the second subset of the cells as the baseline-impedance cells by, for at least one cell of the second subset:

selecting a seed cell that belongs to the second subset and is already designated as one of the baseline-impedance cells, identifying, as a third subset of the cells, other cells of the second subset that are already designated as respective ones of the baseline-impedance cells, and are within a second threshold distance from the seed cell, fitting a line to respective baseline impedances of the third subset of the cells and of the selected seed cell, selecting the cell, based on a distance between the cell and the seed cell being less than a third threshold distance, and subsequently to selecting the cell, designating the cell as one of the baseline-impedance cells, in response to a distance between the representative impedance of the cell and the line being less than a fourth threshold distance.

In some embodiments, the processor is further configured to ascertain that a magnitude of a gradient of the line is less than a threshold gradient-magnitude value, and the processor is configured to select the cell in response to the magnitude of the gradient being less than the threshold gradient-magnitude value.

In some embodiments, the processor is further configured:

to ascertain, subsequently to constructing the BIM, at least one other impedance between the catheter electrode and the external electrode, and to reconstruct the BIM, based on the other impedance.

In some embodiments, the processor is further configured:

to ascertain, using the reconstructed BIM, that the catheter electrode was within the threshold distance of tissue of the heart prior to the BIM having been reconstructed, and to update the map of the tissue, in response to ascertaining that the catheter electrode was within the threshold distance.

In some embodiments, the catheter electrode is a first catheter electrode, the BIM is a first BIM, and the impedances are first impedances, and the processor is further configured:

to ascertain, for each volume of at least some of the different volumes, one or more second impedances between a second catheter electrode, which is in the volume, and the external electrode, to compute a second BIM that at least partly overlaps the first BIM, based on the ascertained second impedances, each of at least some of the baseline-impedance cells of the second BIM having a baseline impedance that is different from the baseline impedance of a corresponding one of the baseline-impedance cells of the first BIM, to ascertain at least one scale factor that scales between the baseline impedances of the first BIM and the baseline impedances of the second BIM, to construct a merged BIM by merging the first BIM with the second BIM, using the ascertained scale factor, to ascertain, using the merged BIM, that the first electrode is within the threshold distance of the tissue, and to ascertain, using the merged BIM, that the second electrode is within the threshold distance of the tissue.

There is further provided, in accordance with some embodiments of the present invention, a method that includes constructing a baseline impedance model (BIM) that models a portion of a heart of a subject as a collection of three-dimensional cells, each of which corresponds to a respective volume within the heart, at least some of the cells being designated as baseline-impedance cells, for each of which the BIM specifies a respective baseline impedance. The method further includes ascertaining, by a processor, an impedance between a catheter electrode, which is within the heart, and an external electrode that is externally coupled to the subject. The method further includes identifying one of the baseline-impedance cells as a reference cell, ascertaining that the catheter electrode is within a threshold distance of tissue of the heart, by comparing the ascertained impedance to the baseline impedance that is specified for the reference cell, and, in response to ascertaining that the catheter electrode is within the threshold distance of the tissue, updating a map of the tissue.

There is further provided, in accordance with some embodiments of the present invention, a method that includes, for each volume of a plurality of different volumes within a heart of a subject, ascertaining, by a processor, one or more impedances between a catheter electrode, which is in the volume, and an external electrode that is externally coupled to the subject. The method further includes constructing a baseline impedance model (BIM) that models a portion of the heart as a collection of three-dimensional cells, each of which corresponds to a respective one of the volumes, by, for each cell of a first subset of the cells, calculating a respective representative impedance, based on the one or more impedances ascertained for the volume to which the cell corresponds, and designating a second subset of the cells, which is a subset of the first subset of the cells, as baseline-impedance cells, each cell of which has, as a respective baseline impedance, the representative impedance of the cell. The method further includes, subsequently to constructing the BIM, ascertaining that the catheter electrode is within a threshold distance of tissue of the heart, based on the baseline impedance of one of the baseline-impedance cells, and, in response to ascertaining that the catheter electrode is within the threshold distance, updating a map of the tissue.

The present invention will be more fully understood from the following detailed description of embodiments thereof, taken together with the drawings, in which:

DETAILED DESCRIPTION OF EMBODIMENTS

Overview

When performing a procedure on a subject using an intracardiac catheter, it is often helpful to know if the catheter is contacting the tissue, or is at least within a given threshold distance of the tissue. Hypothetically, the physician operating the catheter could attempt to ascertain the catheter's proximity to the tissue based on haptic feedback, and/or based on the intensity of any electrocardiographic (ECG) signals acquired by one or more electrodes at the distal end of the catheter. This method, however, might be difficult to implement, particularly for cases in which the catheter comprises a plurality of electrodes, such that the physician would need to separately render a decision regarding the proximity of each of the electrodes. Moreover, even if any ECG signals acquired by the electrodes could be automatically processed to ascertain proximity, some tissue is electrically-inactive, and hence does not allow for ECG-signal acquisition.

Embodiments of the present invention therefore use the impedance between a catheter electrode and another electrode, which is coupled externally to the subject, as an indicator of the proximity of the catheter electrode to the tissue. In general, blood has a lower electrical resistance than tissue, such that, as the catheter electrode approaches the tissue, the real component "Re(Z)" of the impedance "Z" between the catheter electrode and the external electrode increases. Moreover, as the catheter electrode approaches the tissue, the phase "Arg(Z)" of the impedance decreases. Hence, upon registering an Re(Z) value that is sufficiently greater than a baseline Re(Z) value for blood, and/or an Arg(Z) value that is sufficiently less than the baseline Arg(Z) value, it may be ascertained that the catheter electrode is within a threshold distance of the tissue.

Even this method, however, presents a challenge, in that the baseline values may vary with position by an order of magnitude similar to that of the change experienced with tissue proximity. For example, in some locations, proximity to tissue may cause Re(Z) to increase from a baseline value of 95 Ohm to a value of 100 Ohm, whereas in another location, these values may be 90 Ohm and 95 Ohm, respectively. In such a case, upon registering an increase from 90 Ohm to 95 Ohm, it might be difficult to ascertain whether the catheter is near the tissue, or has simply moved to another location within the cavity of the heart having a baseline value of 95 Ohm.

To address this challenge, embodiments of the present invention use the catheter to build a baseline impedance map (BIM), and then use the BIM to ascertain tissue proximity. The BIM models the space within the heart of the subject as a collection of three-dimensional cells (such as cubic cells), and specifies, for at least some of the cells, referred to herein as "baseline-impedance cells," respective baseline impedances. Subsequently, as the catheter is used to perform any relevant procedure within the heart, such as an electroanatomical mapping, the BIM is repeatedly used to ascertain whether any of the electrodes on the catheter is within a threshold distance of the tissue. In particular, the impedance between each of the catheter electrodes and the external electrode is compared to the baseline impedance of the baseline-impedance cell that is closest to the electrode's current location. Based on this comparison, the proximity of the electrode to the tissue is ascertained.

Embodiments described herein also include various techniques for constructing a BIM. For example, embodiments described herein include techniques for the effective designation of baseline-impedance cells, such that the baseline impedance of any given baseline-impedance cell has a high likelihood of being derived solely from blood-impedance values, i.e., solely from impedance values measured while the electrode was not near the tissue of the heart.

Since the catheter electrodes may have varying properties (e.g., size), and the inter-electrode impedance may vary as a function of these properties, a separate BIM may be constructed for each catheter electrode. (Thus, for example, multiple BIMs may be constructed for a catheter having multiple electrodes.) In some embodiments, appropriate scale factors for converting between the baseline impedances of the multiple BIMs are found, and, using these scale factors, the impedances from the BIMs are merged into a single BIM that may be used for any of the electrodes.

System Description

Figure 1:
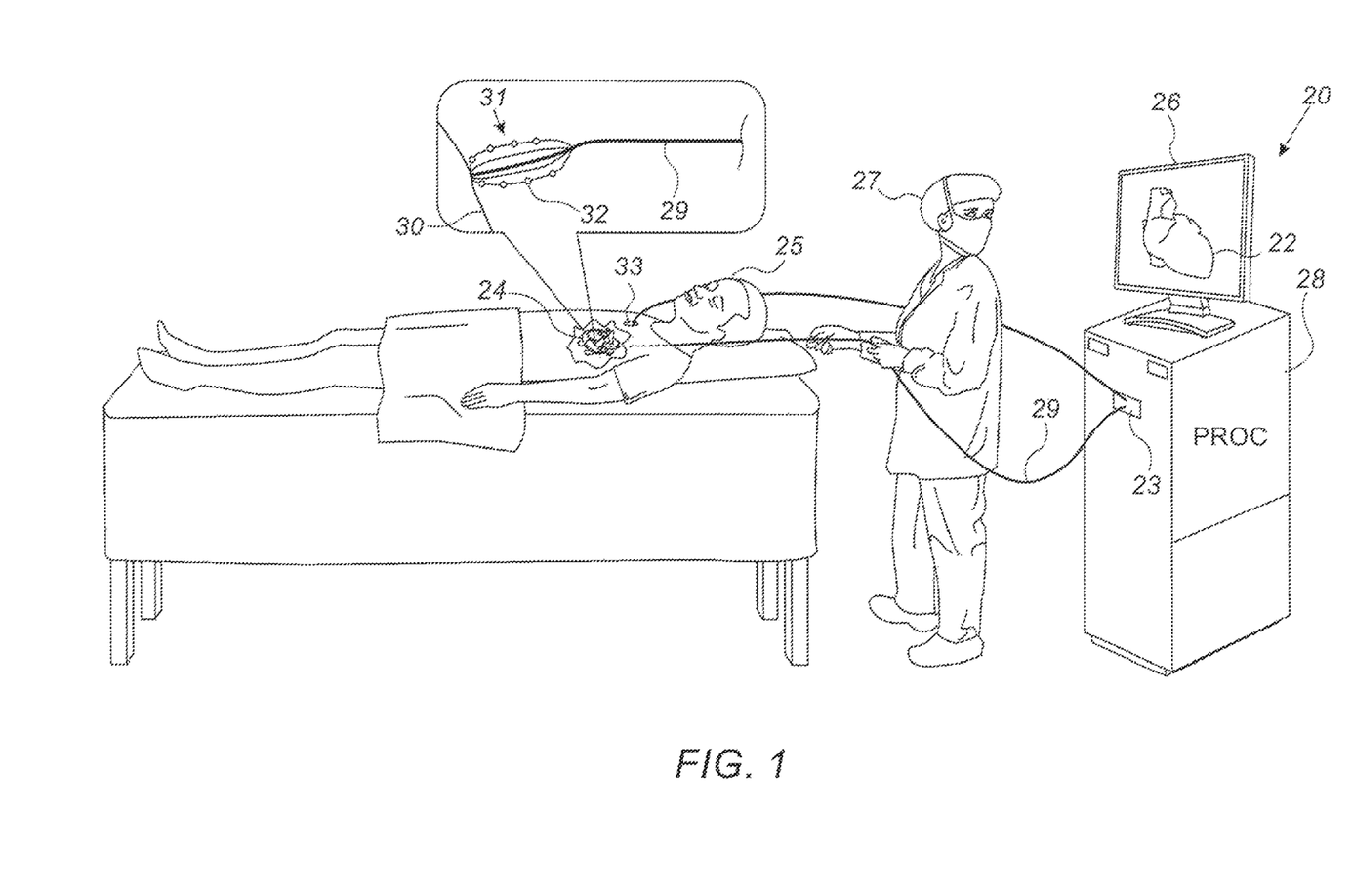
FIG. 1 is a schematic illustration of a system for electro-anatomical mapping, in accordance with some embodiments of the present invention.

Reference is initially made to FIG. 1, which is a schematic illustration of a system 20 for electroanatomical mapping, in accordance with some embodiments of the present invention.

FIG. 1 depicts a physician 27 navigating a catheter 29 within a heart 24 of a subject 25. At various locations along the tissue 30 of heart 24, one or more electrodes 32 at the distal end of catheter 29 record ECG signals from tissue 30. These signals are passed, via catheter 29 and an electrical interface 23 (such as a port or socket), to a processor (PROC) 28. Based on these signals, processor 28 builds an electroanatomical map 22 of the tissue, which maps the anatomical features of the tissue, and additionally associates each of the locations on the tissue with an electrical property, such as a local activation time (LAT), derived from the ECG signals. For example, the processor may color map 22 with various different colors corresponding to different LATs exhibited at different regions of the tissue. During and/or following the mapping procedure, processor 28 may display map 22 on a display 26.

In some embodiments, as shown in FIG. 1, catheter 29 is a basket catheter comprising, at its distal end, a basket 31 of catheter electrodes 32. Alternatively, catheter 29 may have any other suitable form, with electrodes 32 being arranged in any suitable configuration. Catheter 29 typically comprises one or more position sensors (not shown), which allow the processor to track the position of each of electrodes 32. For example, catheter 29 may comprise one or more electromagnetic position sensors, which, in the presence of an external magnetic field, generate signals that vary with the positions of the sensors. Alternatively, to track the position of each electrode 32, the processor may ascertain the respective impedances between the electrode and a plurality of external electrodes coupled externally to subject 25 at various different locations, and then compute the ratios between these impedances. As yet another alternative, the processor may use both electromagnetic tracking and impedance-based tracking, as described, for example, in U.S. Pat. No. 8,456,182, whose disclosure is incorporated herein by reference.

To facilitate the aforementioned impedance-based tracking technique, and/or for constructing and using a BIM as described below, one or more external electrodes 33 are coupled externally to the subject.

In general, processor 28 may be embodied as a single processor, or as a cooperatively networked or clustered set of processors. Processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Constructing and Using a BIM

Figure 2:
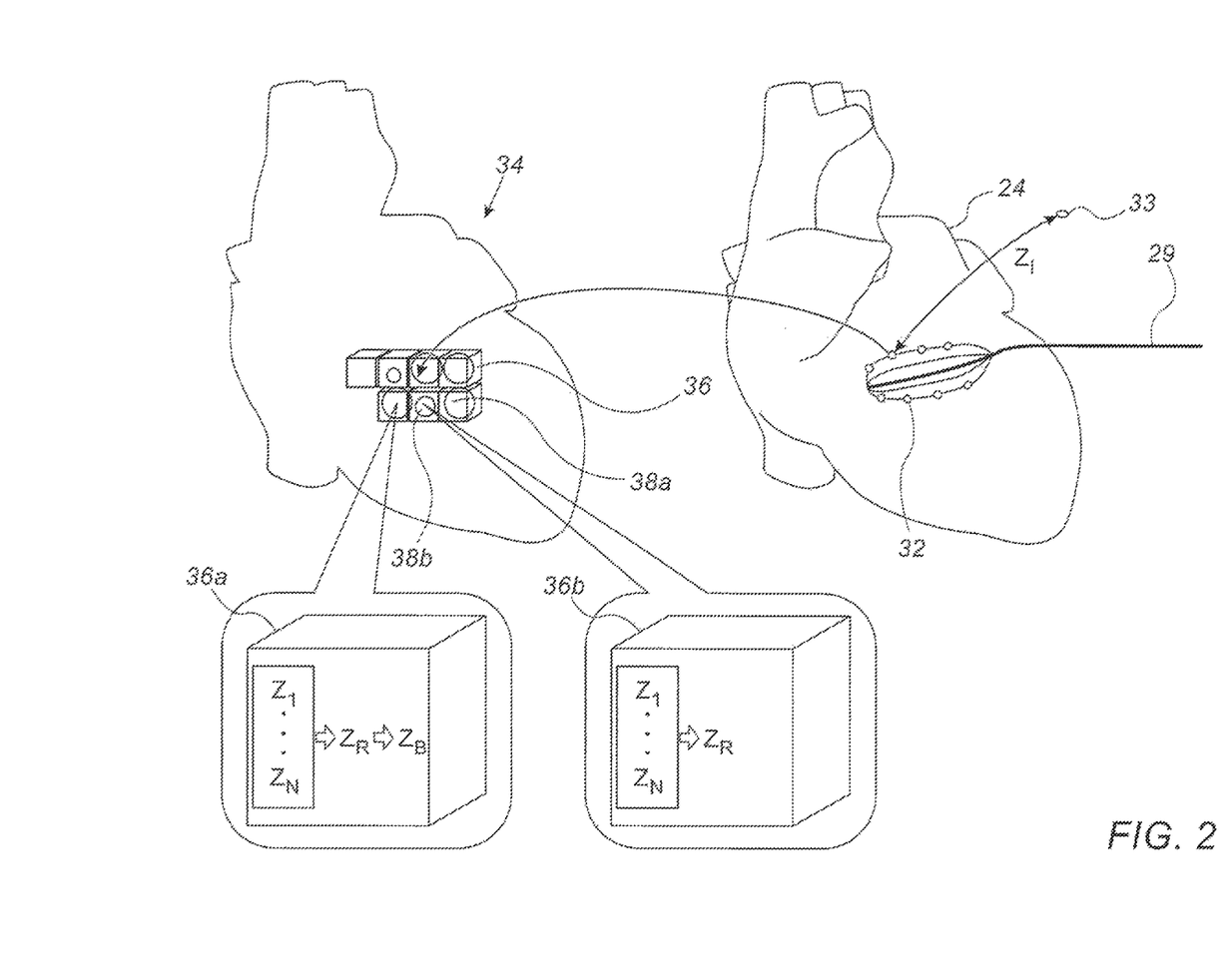
FIG. 2 is a schematic illustration of a baseline impedance map (BIM), in accordance with some embodiments of the present invention.

Reference is now made to FIG. 2, which is a schematic illustration of a BIM 34, in accordance with some embodiments of the present invention.

To facilitate the performance of the electroanatomical mapping procedure illustrated in FIG. 1, or any other relevant type of procedure performed on heart 24, processor 28 constructs BIM 34. BIM 34 models a portion of heart 24, such one or more atria and/or ventricles, as a collection of three-dimensional cells 36. Each cell 36 corresponds to a respective volume within the heart. For example, as illustrated in FIG. 2, each cell 36 may correspond to a cubic volume within the heart. In such a case, the processor may represent the cell in a computer memory with a collection of eight three-dimensional coordinates that constitute the respective corners of the cubic volume. Alternatively or additionally, the processor may represent the cell with the coordinates of the center of the cell, along with the length (or half-length) of the cubic volume. Alternatively, the processor may use any other suitable representation.

Further to constructing BIM 34, the processor may map any given electrode location (ascertained, for example, using any of the techniques described above with reference to FIG. 1) to the BIM, provided that the electrode is within the portion of the heart that is modelled by the BIM. In other words, the processor may ascertain that the location corresponds to a particular cell 36, by ascertaining that the location is included in the volume to which the cell corresponds. For example, an electrode located, per the tracking system of system 20, at (100, 100, 100) would be mapped to a cubic cell that is centered at (99.5, 100, 100) and has a half-length of 1. (Typically, the location of the center of the electrode is used as the location of the electrode, although other conventions may alternatively be used.)

To construct BIM 34 for a particular electrode 32, catheter 29 is moved around within the heart. For each of a plurality of different volumes within the heart within which the electrode is located, processor 28 ascertains one or more (complex) impedances between electrode 32 and external electrode 33. For example, to ascertain each of the impedances for a particular volume, the processor may apply a predetermined voltage between the two electrodes while electrode 32 is in the volume, and then receive via electrical interface 23, from a current sensor coupled to external electrode 33, a signal that indicates the current flowing through external electrode 33. The processor may then compute the magnitude and phase of the impedance from the measured current and predetermined voltage. Alternatively, the processor may apply a predetermined current between the two electrodes, receive, via electrical interface 23, a signal indicating the voltage between the electrodes, and then compute the impedance from the measured voltage and predetermined current.

Each of the impedances $Z_1, \ldots, Z_N$ that is ascertained for a particular volume is stored by the processor in association with the cell that corresponds to the volume. Based on impedances $Z_1, \ldots, Z_N$, the processor may calculate a representative impedance $Z_R$ for the cell. This "representative impedance," or "characteristic impedance," is a single (complex) number that, by virtue of being suitably derived from the ascertained impedances $Z_1, \ldots, Z_N$, characterizes the volume. For example, after removing any outlying impedance values, the processor may calculate the representative impedance of the cell by averaging the remaining impedances. To remove the outliers, the processor may, for example, sort the impedances by both their real and imaginary components, and then remove any of the impedances that fall within a given top or bottom percentile of either one of the sorted lists.

Typically, the processor requires a certain minimum number of (non-outlier) impedances for a cell, in order to calculate $Z_R$ for the cell. Those of the cells that have this minimum number of observations, and hence a representative impedance as calculated by the processor, are referred to herein as "representative-impedance cells." (Representative-impedance cells constitute a subset of the cells in BIM 34, i.e., at least some of the cells in BIM 34 are representative-impedance cells.)

As further described below, at least some of the representative-impedance cells may be used as baseline-impedance cells, in that tissue proximity may be ascertained in response to a measured impedance differing from the representative impedance of one of these baseline-impedance cells. For example, using any of the techniques described below with reference to FIG. 3, the processor may identify a subset of the representative-impedance cells that the processor assumes, with a relatively high degree of confidence, have representative impedances derived solely from blood-impedance values. These cells are designated by BIM 34 as "baseline-impedance cells" 36a. Each baseline-impedance cell 36a has, as a respective baseline impedance $Z_B$, the representative impedance of the cell.

(Purely by way of illustration, FIG. 2 indicates each baseline-impedance cell 36a by displaying a sphere within the cell; in particular, a larger sphere 38a is used to indicate each baseline-impedance cell, while a smaller sphere 38b is used to indicate each of the remaining representative-impedance cells 36b. Those of the cells that are not representative-impedance cells are drawn without any marker.)

It is noted that, due to the beating of the heart, some volumes that contain only blood most of the time may occasionally contain tissue, such that some of the impedance values obtained for these volumes may be tissue-impedance values. These tissue-impedance values may be removed, however, using the outlier-removal techniques described above, such that even the cells that correspond to such volumes may be designated as baseline-impedance cells. Alternatively or additionally, during the recording of the impedance values for any of these volumes, the processor may ignore any impedance value that is greater than a preceding value by more than a threshold, since such a jump in impedance indicates tissue contact. (In other words, the processor may refrain from adding certain outliers to the BIM data in the first place, such as to obviate the need to later remove these outliers.)

Subsequently to constructing BIM 34, the processor may use the BIM, e.g., during an electroanatomical mapping procedure, to ascertain whether any of electrodes 32 is within a threshold distance of tissue of the heart. To perform this ascertainment, the processor identifies a baseline-impedance cell 36a that corresponds to the electrode's current location (by virtue of corresponding to a volume that contains the location), or at least corresponds to a volume that is closer to the location than any other volume to which any other of the baseline-impedance cells corresponds, as a reference cell. (This correspondence is indicated in FIG. 2 by the arrow that points from a particular electrode in heart 24 to a particular baseline-impedance cell in BIM 34.) The processor also ascertains the impedance $Z_I$ between the electrode and external electrode 33, and then compares $Z_I$ to the baseline impedance $Z_B$ that is specified for the reference cell. If $Z_I$ differs from $Z_B$ in a manner that indicates tissue proximity, the processor may ascertain that the electrode is in contact with, or is at least within a threshold distance of, the tissue of the heart.

To find a suitable reference cell, the processor may calculate the distances between the electrode's location and the respective centers of the baseline-impedance cells, i.e., the distances between the electrode's location and the respective locations to which the centers of the baseline-impedance cells correspond. The processor may then find the minimum of these distances, and, if this minimum distance is less than a suitable threshold distance, identify the corresponding baseline-impedance cell, whose center is closer to the electrode's location than any other center, as the reference cell. The processor may then compare $Z_I$ to $Z_B$ of the reference cell, e.g., by computing the ratio $Re(Z_I)/Re(Z_B)$ and comparing this ratio to a first threshold, and/or by computing the phase difference $Arg(Z_I)-Arg(Z_B)$ and comparing this difference to a second threshold. (The first threshold may, for example, be between 1.03 and 1.05, while the second threshold may, for example, be between 1 and 2 degrees.) If the ratio is greater than the first threshold, and/or if the difference is less than the second threshold, the processor may ascertain that the electrode is proximate to—i.e., is in contact with, or is at least within a threshold distance of—the tissue of the heart.

Further to ascertaining proximity of the electrode to the tissue of the heart, the processor may update map 22 to incorporate the location of the electrode, and/or to incorporate information contained in an ECG signal acquired by the electrode. Alternatively or additionally, the processor may display, on display 26, an indication that the electrode is near the tissue, e.g., by displaying an icon that represents the distal end of the catheter, in which the electrodes that are proximate to the tissue are colored differently from the other electrodes. Alternatively or additionally, the processor may perform any other relevant function.

Typically, after initializing the BIM, while the procedure is in progress, the processor repeatedly updates the BIM by adding any newly-ascertained impedances to the measurements that have been collected thus far, and then reconstructing the BIM based on all of the measurements, including the newly-ascertained impedances. For example, after adding one or more impedances to the collected measurements, the processor may calculate $Z_R$ for any cells that have new impedance values, and then, based on these new $Z_R$ values, re-designate the set of baseline-impedance cells in the BIM.

Alternatively or additionally, the processor may periodically, e.g., once every second, reconstruct the entire BIM, in order to account for any newly-acquired impedances. In other words, the processor may periodically (i) define the collection of cells 36, (ii) pass through the entire collection of cells 36, computing $Z_R$ for each of the cells that has a sufficient number of non-outlier impedance measurements, and (iii) designate at least some of the representative-impedance cells as baseline-impedance cells. In defining the collection of cells, the processor may include some cells that were not previously part of the BIM, but were added as a result of the catheter passing through some volumes of the heart for the first time. Similarly, in designating the baseline-impedance cells, the processor may include some cells that were not previously designated as baseline-impedance cells, and/or remove some cells that were previously designated as baseline-impedance cells.

Designating Baseline-Impedance Cells

Figure 3:
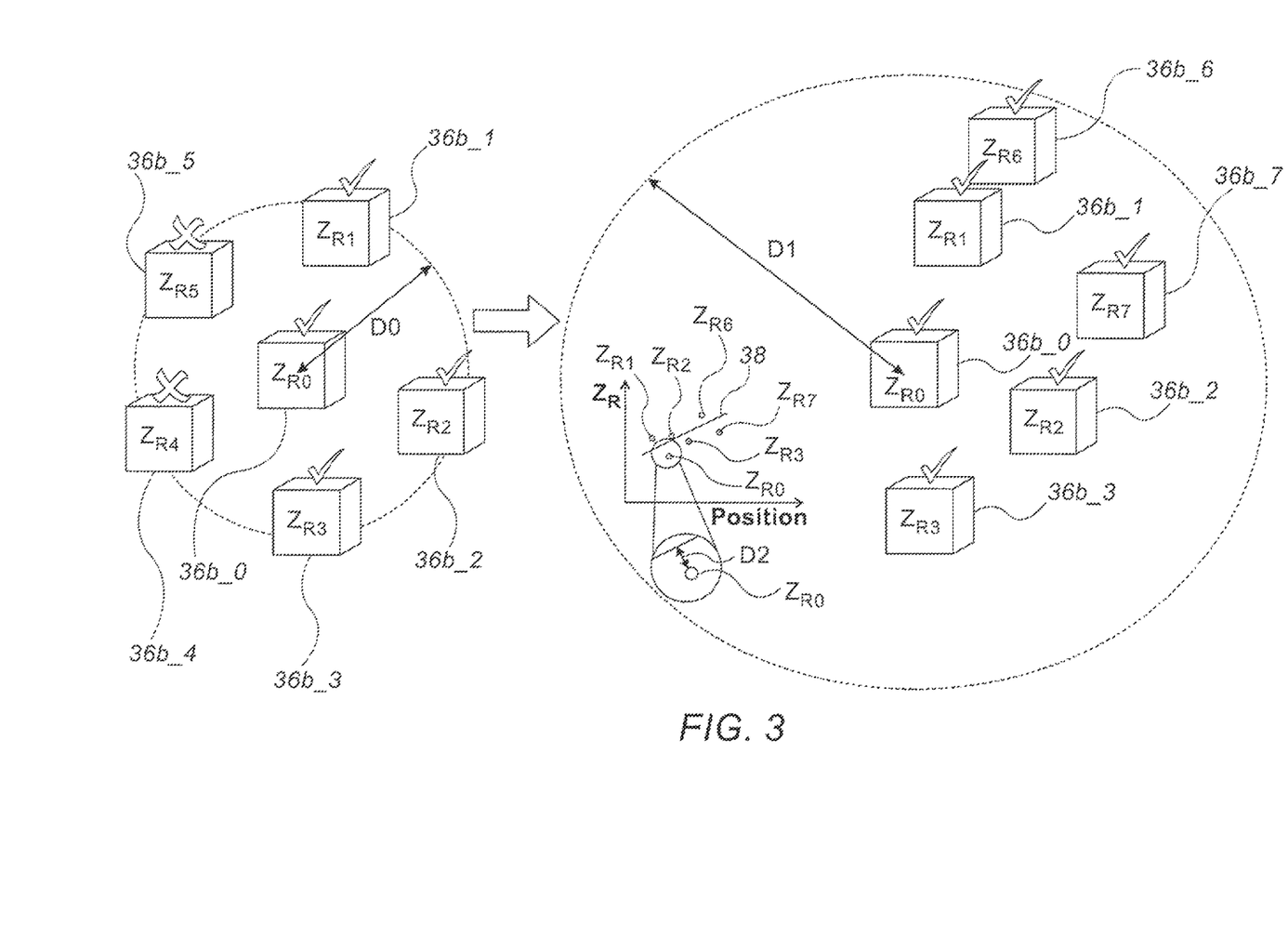
FIG. 3 is a schematic illustration of a method for designating a representative-impedance cell as a baseline-impedance cell, in accordance with some embodiments of the present invention.

Reference is now made to FIG. 3, which is a schematic illustration of a method for designating a representative-impedance cell as a baseline-impedance cell, in accordance with some embodiments of the present invention.

As described above with reference to FIG. 2, after designating representative-impedance cells 36b by calculating representative impedances $Z_R$ for these cells, the processor designates at least some of the representative-impedance cells as baseline-impedance cells. FIG. 3 illustrates one possible technique that may be used to perform this latter designation, for a particular hypothetical representative-impedance cell 36b_0 having a representative impedance $Z_{RO}$. Per this technique, as shown at the left of FIG. 3, the processor identifies neighboring representative-impedance cells that are within a threshold distance D0 from cell 36b_0. (The distance between two cells is typically measured between the respective centers of the cells.) In the example shown in FIG. 3, this subset of cells 36 consists of five cells: a first neighbor cell 36b_1 having a representative impedance $Z_{R1}$, a second neighbor cell 36b_2 ($Z_{R2}$), a third neighbor cell 36b_3 ($Z_{R3}$), a fourth neighbor cell 36b_4 ($Z_{R4}$), and a fifth neighbor cell 36b_5 ($Z_{R5}$). (It is noted that, for simplicity, FIG. 3 depicts the neighborhood of cell 36b_0 in two dimensions, whereas, in practice, the neighborhood of cell 36b_0 is three-dimensional.)

Next, the processor designates cell 36b_0 as a potential baseline-impedance cell, based on the respective representative impedances of the neighboring cells. In general, a "potential baseline-impedance cell" is a cell having a $Z_R$ value that is likely derived solely from blood-impedance values. One indication for this is that the representative impedance of the cell is similar to that of its neighbors. Another indication is that the neighbors of the cell have similar representative impedances. The processor may look for one or both of these indications, before labeling cell 36b_0 as a potential baseline-impedance cell. That is, the processor may calculate at least one measure of similarity between $Z_{R0}$ and $Z_{R1}, \ldots, Z_{R5}$, and/or at least one measure of variation of $Z_{R1}, \ldots, Z_{R5}$. The processor may then designate cell 36b0 as a potential baseline-impedance cell, in response to the measure of similarity and the measure of variation.

For example, the processor may calculate the following two measures of similarity between $Z_{R0}$ and $Z_{R1}, \ldots, Z_{R5}$:

$$MR = |Re(Z_{R0}) - mr|; \text{ and}$$

$$MI = |Im(Z_{R0}) - mi|,$$

where $Re(Z)$ and $Im(Z)$ are, respectively, the real and imaginary components of any impedance Z, mr=Median(Re $(Z_{R1}), \ldots, Re(Z_{R5}))$, and mi=Median(Im$(Z_{R1}), \ldots,$ Im$(Z_{R5})$). The processor may also calculate the following two measures of variation of $Z_{R1}, \ldots, Z_{R5}$:

$$VR = \text{Median}(|Re(Z_{R1}) - mr|, \ldots, |Re(Z_{R5}) - mr|); \text{ and}$$

$$VI = \text{Median}(|Im(Z_{R1}) - mi|, \ldots, |Im(Z_{R5}) - mi|).$$

The processor may then compare each of MR, MI, VR, and VI to a different respective threshold, and then designate cell 36b_0 as a potential baseline-impedance cell only if each of these four quantities is less than its corresponding threshold. (The threshold for MR may be predetermined, or may be derived from VR; likewise, the threshold for MI may be predetermined, or may be derived from VI.)

After passing through all of the representative-impedance cells and designating at least some of these cells as potential baseline-impedance cells, the processor passes through the potential baseline-impedance cells, and designates at least some of these cells as baseline-impedance cells. For example, with reference to FIG. 3, it will be assumed that cell 36b_0, along with those of cells 36b_1, . . ., 36b_5 similarly marked with a checkmark, were designated as potential baseline-impedance cells. Subsequently to designating these cells as potential baseline-impedance cells, the processor may determine whether cell 36b_0 should be designated as a baseline-impedance cell, as described below.

By way of introduction, at a general level, the criteria for designating a given cell as a baseline-impedance cell are similar to the criteria for designating the cell as a potential baseline-impedance cell: similarity of the cell to its neighbors, and/or low inter-neighbor variation. However, as explained below, the specific techniques that the processor may perform to test for high similarity and low variation may be different from the techniques described above. Moreover, the processor may consider a larger neighborhood than was considered before, and/or may consider only those neighbors that are similarly designated as potential baseline-impedance cells.

For example, as shown at the right of FIG. 3, the processor may identify another subset of cells 36, consisting of other representative-impedance cells that are also designated as potential baseline-impedance cells, and are within a threshold distance D1 of cell 36b_0. (As implied above, D1 may be greater than D0.) In the specific case shown in FIG. 3, this subset consists of cells 36b_1, . . . , 36b_3, along with another cell 36b_6, having a representative impedance of $Z_{R6}$, and another cell 36b_7, having a representative impedance of $Z_{R7}$. Based on the neighbor-impedances $Z_{R1}, \ldots, Z_{R3}, Z_{R6},$ and $Z_{R7}$, the processor may designate cell 36b_0 as a baseline impedance cell. For example, the processor may calculate at least one measure of similarity between $Z_{R0}$ and the neighbor-impedances, such as one or both of the MR and MI measures described above, and then designate cell 36b_0 as a baseline impedance cell in response to this measure, e.g., in response to MR and/or MI being less than a threshold.

Alternatively or additionally, the processor may fit a line 38 to the neighbor-impedances. Typically, line 38 is defined by the equation $Z_R = Ax + By + Cz + D$, where $Z_R$ is the representative impedance, and (x, y, z) are the coordinates of the center of cell. Given the representative impedances and the center-coordinates of the neighbors, the processor finds the values of A, B, C, and D that best fit the observations. (In FIG. 3, for sake of illustration, the three independent variables—x, y, and z—are reduced to a single "Position" variable.) The processor then compares the distance D2 between $Z_{R0}$ and line 38 a threshold distance. If D2 is less than this threshold, the processor may designate cell 36b_0 as a baseline impedance cell.

Figure 4:
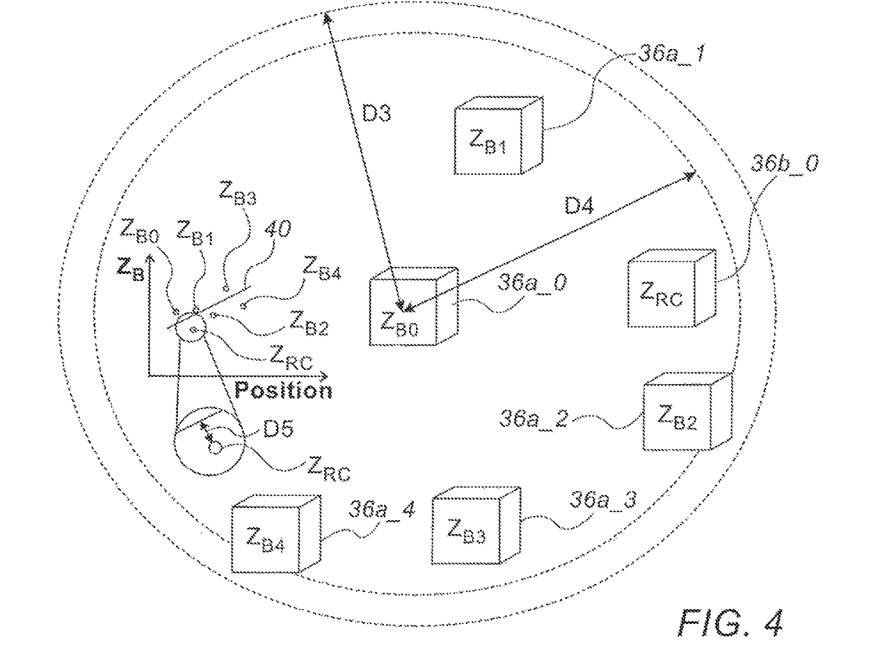
FIG. 4 is a schematic illustration of a method for further designation of baseline-impedance cells, in accordance with some embodiments of the present invention.

Reference is now made to FIG. 4, which is a schematic illustration of a method for further designation of baseline-impedance cells, in accordance with some embodiments of the present invention.

After designating an initial pool of baseline-impedance cells as described above with reference to FIG. 3, the processor may execute a "region-growing" procedure, whereby the processor repeatedly removes a "seed" baseline-impedance cell from the pool, and then adds suitable neighbors of the seed cell, which were not yet designated as baseline-impedance cells, to the pool, until no more baseline-impedance cells remain in the pool. The processor may thus designate additional baseline-impedance cells.

One example technique for region-growing is illustrated in FIG. 4. FIG. 4 assumes that the processor has selected a particular seed cell 36a_0, which was already designated as a baseline-impedance cell, from the pool of baseline-impedance cells. The processor may then use seed cell 36a_0 to designate other, neighboring cells as additional baseline-impedance cells. To do this, the processor may first identify a subset of cells 36 that are already designated as baseline-impedance cells, and are within a threshold distance D3 from seed cell 36a_0. Next, the processor may fit a line to the baseline impedances of the identified subset of cells and of the seed cell. (This fitting may be performed, for example, as described above with reference to line 38 of FIG. 3.) FIG. 4 thus shows a line 40 fit to a plurality of baseline impedances: $Z_{B0}$, which belongs to seed cell 36a_0, and $Z_{B1}, Z_{B2}, Z_{B3},$ and $Z_{B4}$, which belong to, respectively, neighbor baseline-impedance cells 36a_1, 36a_2, 36a_3, and 36a_4.

The processor may also select any "candidate" representative-impedance cells that are not yet designated as baseline-impedance cells, and are at a distance from the seed cell that is less than a threshold distance D4, which may be less than D3. (The candidate representative-impedance cells need not necessarily be potential baseline-impedance cells.) FIG. 4 shows one such selected candidate, a candidate cell 36b_0 having a representative impedance $Z_{RC}$. Subsequently to selecting cell 36b_0, the processor compares the distance D5 between $Z_{RC}$ and line 40 to a threshold. If this distance is less than the threshold, the processor designates cell 36b_0 as a new baseline-impedance cell, and then adds this new baseline-impedance cell to the pool. The processor then selects the next seed cell from the pool.

Since a large gradient of line 40 typically indicates that the neighborhood of the seed cell is relatively close to tissue, the processor typically does not select any candidate cells for a given seed cell unless the magnitude of the gradient of line 40 is less than a threshold value. In other words, in selecting a candidate cell, the processor typically first ascertains that the magnitude of the gradient of the fit line is less than the threshold, and then selects the candidate cell responsively thereto.

Merging Multiple BIMs

Figure 5:
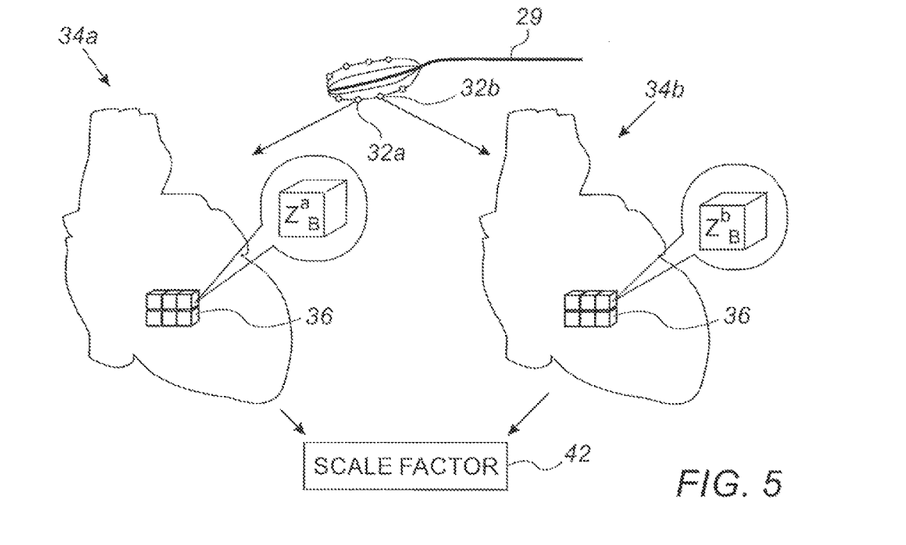
FIG. 5 is a schematic illustration of a technique for merging multiple BIMs, in accordance with some embodiments of the present invention.

Reference is now made to FIG. 5, which is a schematic illustration of a technique for merging multiple BIMs, in accordance with some embodiments of the present invention.

As described above in the Overview, the impedance between a given catheter electrode 32 and external electrode 33 may be a function of the size, and/or other properties, of electrode 32. Hence, the processor typically constructs a separate BIM for each respective electrode 32, using the BIM-construction techniques described above. For example, FIG. 5 illustrates a first BIM 34a, constructed for a first electrode 32a, and a second BIM 34b, constructed for a second electrode 32b having different properties from those of first electrode 32a. BIMs 34a and 34b overlap at least in part, i.e., the portion of the heart modeled by first BIM 34a at least partly overlaps the portion of the heart modeled by second BIM 34b, such that at least some cells of BIM 34a correspond to the same respective volumes as do some cells of BIM 34b. Due to the differences between the electrodes, however, the impedances measured by the processor, and hence the baseline impedances calculated by the processor, vary between the two BIMs in the region of overlap, such that each of at least some of the baseline-impedance cells of second BIM 24b have a baseline impedance $Z^b_B$ that is different from the baseline impedance $Z^a_B$ of the corresponding baseline-impedance cell of first BIM 24a. (In this context, two cells are said to correspond to one another if the two cells correspond to the same volume of the heart.)

Although the processor may continue using (and updating) a different respective BIM for each electrode, the processor typically merges BIMs together whenever possible. Since a merged BIM includes more information than does either one of the individual BIMs from which it was constructed, the merged BIM is typically more helpful for assessing tissue proximity, relative to either one of the original BIMs.

For example, as the electroanatomical mapping procedure proceeds, the processor may repeatedly assess the overlap between various pairs of the BIMs that have been constructed thus far. Upon identifying that two given BIMs overlap by at least a threshold number of baseline-impedance cells, the processor may merge the two BIMs, using the techniques described below. In this manner, the processor may repeatedly merge different pairs of BIMs, until the processor computes a single merged BIM, which incorporates impedances from all of the electrodes.

To merge two given BIMs, the processor first ascertains at least one scale factor 42 that scales between the baseline impedances of the BIMs, and then uses the scale factor to merge the BIMs. For example, with reference to FIG. 5, the processor may find the value $\hat{c}$ of the variable "c" that minimizes the function $\Sigma_{i \in G}(Z_{Bi}^a - c Z_{Bi}^b)^2$, where G is the set of all baseline-impedance cells that correspond to the same volume in BIMs 34a and 34b (i.e., G is the region in which the two BIMs overlap), $Z_{Bi}^a$ is the baseline impedance of the $i^{th}$ cell in G in first BIM 34a, and $Z_{Bi}^b$ is the baseline impedance of the $i^{th}$ cell in G in second BIM 34b. The processor may then multiply the impedances in second BIM 34b by $\hat{c}$, and then incorporate these scaled impedances into first BIM 34a. Alternatively, the processor may, by minimizing the function $\Sigma_{i \in G}(c_1 Z_{Bi}^a - c_2 Z_{Bi}^b)^2$ under an appropriate constraint (such as $c_1 + c_2 = 2$), ascertain two scale factors $\hat{c_1}$ and $\hat{c_2}$ that collectively scale between the baseline impedances. The processor may then merge the two BIMs by multiplying the impedances in first BIM 34a by $\hat{c_1}$ and the impedances in second BIM 34b by $\hat{c_2}$, and then incorporating all of these scaled impedances into the merged BIM.

Subsequently to computing a merged BIM, the processor may use the merged BIM to ascertain the tissue proximity of any one of the electrodes that contributed to the merged BIM. For example, assuming that, as described above, the merged BIM includes first BIM 34a scaled by $\hat{c_1}$ and second BIM 34b scaled by $\hat{c_2}$, the processor may multiply any measured impedance "$Z_1$" between first electrode 32a and the external electrode by $\hat{c_1}$, and then compare the resulting product $Z_1 * \hat{c_1}$ to the relevant baseline impedance in the merged BIM. Similarly, for second electrode 32b, the processor may multiply any measured impedance "$Z_2$" by $\hat{c_2}$, and then compare the resulting product $Z_2 * \hat{c_2}$ to the relevant baseline impedance.

Performing an Electroanatomical Mapping

Figure 6:
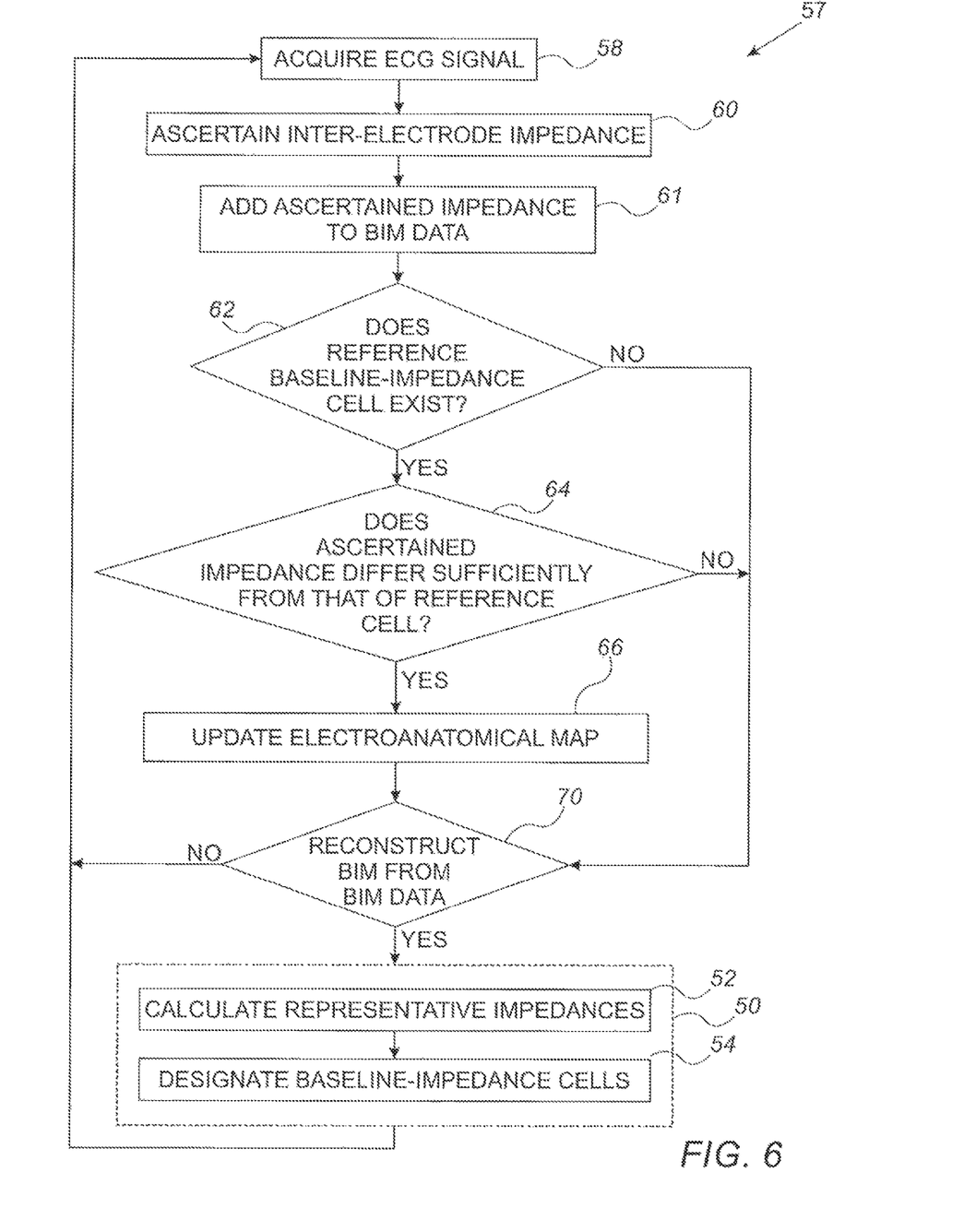
FIG. 6 is a flow diagram for a method for performing an electroanatomical mapping using a BIM, in accordance with some embodiments of the present invention.

Reference is now made to FIG. 6, which is a flow diagram for a method 57 for performing an electroanatomical mapping using a BIM, in accordance with some embodiments of the present invention. Method 57 is performed by processor 28 for each catheter electrode, while the physician moves the catheter around within the heart of the subject.

Method 57 begins with an ECG-signal-acquiring step 58, at which the catheter electrode acquires an ECG signal. Next, the processor ascertains the inter-electrode impedance between the catheter electrode and an external electrode, at an impedance-ascertaining step 60. (Impedance-ascertaining step 60 may alternatively take place before or during ECG-signal-acquiring step 58.) Next, at an impedance-adding step 61, the processor adds the newly-ascertained impedance to the BIM data (i.e., to the measurements that have been collected thus far), by storing the ascertained impedance in association with the appropriate BIM cell.

Next, using the ascertained inter-electrode impedance, the processor checks whether the BIM indicates that the catheter electrode is within a threshold distance of the tissue. In particular, at a reference-cell-seeking step 62, the processor first looks for a suitable reference baseline-impedance cell. If a suitable reference cell is found, the processor next checks, at an impedance-comparing step 64, whether the ascertained impedance differs sufficiently from the baseline impedance of the reference cell, such that the electrode may be deemed to be proximate to tissue. If yes, the processor updates the electroanatomical map to incorporate the acquired ECG signal and/or the location of the electrode, at a map-updating step 66.

Following map-updating step 66, the processor checks, at a checking step 70, whether the BIM should be reconstructed from the BIM data. For example, the processor may check whether a certain minimum number of newly-ascertained impedances have been added to the BIM data, and/or whether a certain period of time has gone by since the last BIM construction. If the processor decides the BIM should be reconstructed, the processor reconstructs the BIM at a BIM-reconstructing step 50, by first calculating the representative impedances at a representative-impedance-calculating sub-step 52, and then designating the baseline-impedance cells at a baseline-impedance-cell designating sub-step 54.

If the processor ascertains that the BIM does not indicate that the catheter electrode is within the threshold distance—either by virtue the ascertained impedance not differing sufficiently from the baseline impedance of the reference cell, or by virtue of no suitable reference cell being found—the processor does not update the electroanatomical map, but rather, proceeds directly to checking step 70.

Subsequently to BIM-reconstructing step 50, or if no BIM reconstruction is performed subsequently to checking step 70, the processor returns to ECG-signal-acquiring step 58, and then repeats the above-described series of steps.

In some embodiments, following BIM-reconstructing step 50, the processor iterates over at least some impedance values that were previously acquired and incorporated into the BIM, and, by performing reference-cell-seeking step 62 and impedance-comparing step 64, identifies any of these values that, in light of the reconstructed BIM, indicate proximity to tissue. In other words, using the reconstructed BIM, the processor may ascertain that the catheter electrode was proximate to the tissue prior to the BIM having been reconstructed, but, due to the previous, less-comprehensive state of the BIM, this proximity was not identified. In response to ascertaining that the catheter electrode was proximate to the tissue, the processor may update the map of the tissue to incorporate the electrode's location at the time the impedance value was acquired, and/or an ECG signal acquired by the electrode at the location, and may further remove the relevant cell from the BIM.

In some embodiments, if a BIM has not yet been initialized, or if each of the catheter electrodes is more than a particular distance from the nearest baseline-impedance cell, the processor indicates as such to the physician, so the physician knows not to expect any indications of tissue proximity. For example, the processor may display a message on display 26, indicating that a BIM has not yet been initialized, or that the catheter is too far from the BIM.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
an electrical interface; and
a processor, configured:
to construct a baseline impedance model (BIM) that models a portion of a heart of a subject as a collection of three-dimensional cells, each of which corresponds to a respective volume within the heart, at least some of the cells being designated as baseline-impedance cells, for each of which the BIM specifies a respective baseline impedance,
to ascertain, based on a signal received via the electrical interface, an impedance between a catheter electrode, which is within the heart, and an external electrode that is externally coupled to the subject,
to identify one of the baseline-impedance cells as a reference cell,
to ascertain that the catheter electrode is within a threshold distance of tissue of the heart, by comparing the ascertained impedance to the baseline impedance that is specified for the reference cell, and
to update a map of the tissue, in response to ascertaining that the catheter electrode is within the threshold distance of the tissue.

2. The apparatus according to claim 1, wherein the processor is configured to update the map of the tissue to incorporate a location of the catheter electrode, in response to ascertaining that the catheter electrode is within the threshold distance of the tissue.

3. The apparatus according to claim 1, wherein the processor is configured to update the map of the tissue to incorporate information contained in an electrocardiographic signal acquired by the electrode, in response to ascertaining that the catheter electrode is within the threshold distance of the tissue.

4. The apparatus according to claim 1, wherein the processor is configured to identify the one of the baseline-impedance cells as the reference cell in response to a center of the one of the baseline-impedance cells corresponding to a location that is closer to a location of the catheter electrode than is any other location to which a center of any other one of the baseline-impedance cells corresponds.

5. The apparatus according to claim 4, wherein the processor is configured to identify the one of the baseline-impedance cells as the reference cell in response to the location of the catheter electrode being included in the volume to which the one of the baseline-impedance cells corresponds.

6. The apparatus according to claim 1, wherein the processor is configured to compare the ascertained impedance to the baseline impedance that is specified for the reference cell by:
computing a ratio between a real component of the ascertained impedance and a real component of the baseline impedance, and
comparing the ratio to a ratio threshold.

7. The apparatus according to claim 1, wherein the processor is configured to compare the ascertained impedance to the baseline impedance that is specified for the reference cell by:
computing a difference between a phase of the ascertained impedance and a phase of the baseline impedance, and
comparing the difference to a phase-difference threshold.

8. Apparatus, comprising:
an electrical interface; and
a processor, configured:
to ascertain, for each volume of a plurality of different volumes within a heart of a subject, one or more impedances between a catheter electrode, which is in the volume, and an external electrode that is externally coupled to the subject, based on a signal received via the electrical interface,
to construct a baseline impedance model (BIM) that models a portion of the heart as a collection of three-dimensional cells, each of which corresponds to a respective one of the volumes, by:
for each cell of a first subset of the cells, calculating a respective representative impedance, based on the one or more impedances ascertained for the volume to which the cell corresponds, and
designating a second subset of the cells, which is a subset of the first subset of the cells, as baseline-impedance cells, each cell of which has, as a respective baseline impedance, the representative impedance of the cell, to ascertain, subsequently to constructing the BIM, that the catheter electrode is within a threshold distance of tissue of the heart, based on the baseline impedance of one of the baseline-impedance cells, and to update a map of the tissue, in response to ascertaining that the catheter electrode is within the threshold distance.

9. The apparatus according to claim 8, wherein the processor is configured to calculate the representative impedance of the cell by averaging at least some of the impedances ascertained for the volume to which the cell corresponds.

10. The apparatus according to claim 8, wherein the threshold distance is a first threshold distance, and wherein the processor is configured to designate the second subset of the cells as the baseline-impedance cells by, for at least one cell of the second subset:

identifying, as a third subset of the cells, other cells of the first subset that are within a second threshold distance from the cell, designating the cell as a potential baseline-impedance cell, based on respective representative impedances of the third subset of the cells, subsequently to designating the cell as a potential baseline-impedance cell, identifying, as a fourth subset of the cells, other cells of the first subset that are also designated as potential baseline-impedance cells, and are within a third threshold distance from the cell, and designating the cell as one of the baseline-impedance cells, based on respective representative impedances of the fourth subset of the cells.

11. The apparatus according to claim 10, wherein the processor is configured to designate the cell as a potential baseline-impedance cell by:

calculating at least one measure of similarity between the representative impedance of the cell and the respective representative impedances of the third subset of the cells, calculating at least one measure of variation of the respective representative impedances of the third subset of the cells, and designating the cell as a potential baseline-impedance cell in response to the measure of similarity and the measure of variation.

12. The apparatus according to claim 10, wherein the processor is configured to designate the cell as one of the baseline-impedance cells by:

calculating at least one measure of similarity between the representative impedance of the cell and the respective representative impedances of the fourth subset of the cells, and designating the cell as one of the baseline-impedance cells in response to the measure of similarity.

13. The apparatus according to claim 10, wherein the processor is configured to designate the cell as one of the baseline-impedance cells by:

fitting a line to the respective representative impedances of the fourth subset of the cells, and designating the cell as one of the baseline-impedance cells, in response to a distance between the representative impedance of the cell and the line being less than a fourth threshold distance.

14. The apparatus according to claim 8, wherein the threshold distance is a first threshold distance, and wherein the processor is configured to designate the second subset of the cells as the baseline-impedance cells by, for at least one cell of the second subset:

selecting a seed cell that belongs to the second subset and is already designated as one of the baseline-impedance cells, identifying, as a third subset of the cells, other cells of the second subset that are already designated as respective ones of the baseline-impedance cells, and are within a second threshold distance from the seed cell, fitting a line to respective baseline impedances of the third subset of the cells and of the selected seed cell, selecting the cell, based on a distance between the cell and the seed cell being less than a third threshold distance, and subsequently to selecting the cell, designating the cell as one of the baseline-impedance cells, in response to a distance between the representative impedance of the cell and the line being less than a fourth threshold distance.

15. The apparatus according to claim 14, wherein the processor is further configured to ascertain that a magnitude of a gradient of the line is less than a threshold gradient-magnitude value, and wherein the processor is configured to select the cell in response to the magnitude of the gradient being less than the threshold gradient-magnitude value.

16. The apparatus according to claim 8, wherein the processor is further configured:

to ascertain, subsequently to constructing the BIM, at least one other impedance between the catheter electrode and the external electrode, and to reconstruct the BIM, based on the other impedance.

17. The apparatus according to claim 16, wherein the processor is further configured:

to ascertain, using the reconstructed BIM, that the catheter electrode was within the threshold distance of tissue of the heart prior to the BIM having been reconstructed, and to update the map of the tissue, in response to ascertaining that the catheter electrode was within the threshold distance.

18. The apparatus according to claim 8, wherein the catheter electrode is a first catheter electrode, the BIM is a first BIM, and the impedances are first impedances, and wherein the processor is further configured:

to ascertain, for each volume of at least some of the different volumes, one or more second impedances between a second catheter electrode, which is in the volume, and the external electrode, to compute a second BIM that at least partly overlaps the first BIM, based on the ascertained second impedances, each of at least some of the baseline-impedance cells of the second BIM having a baseline impedance that is different from the baseline impedance of a corresponding one of the baseline-impedance cells of the first BIM, to ascertain at least one scale factor that scales between the baseline impedances of the first BIM and the baseline impedances of the second BIM, to construct a merged BIM by merging the first BIM with the second BIM, using the ascertained scale factor, to ascertain, using the merged BIM, that the first electrode is within the threshold distance of the tissue, and to ascertain, using the merged BIM, that the second electrode is within the threshold distance of the tissue.

19. A method, comprising:
constructing a baseline impedance model (BIM) that models a portion of a heart of a subject as a collection of three-dimensional cells, each of which corresponds to a respective volume within the heart,
at least some of the cells being designated as baseline-impedance cells, for each of which the BIM specifies a respective baseline impedance;
ascertaining, by a processor, an impedance between a catheter electrode, which is within the heart, and an external electrode that is externally coupled to the subject;
identifying one of the baseline-impedance cells as a reference cell;
ascertaining that the catheter electrode is within a threshold distance of tissue of the heart, by comparing the ascertained impedance to the baseline impedance that is specified for the reference cell; and
in response to ascertaining that the catheter electrode is within the threshold distance of the tissue, updating a map of the tissue.

20. The method according to claim 19, wherein updating the map of the tissue comprises updating the map of the tissue to incorporate a location of the catheter electrode.

21. The method according to claim 19, wherein updating the map of the tissue comprises updating the map of the tissue to incorporate information contained in an electrocardiographic signal acquired by the electrode.

22. The method according to claim 19, wherein identifying the one of the baseline-impedance cells as the reference cell comprises identifying the one of the baseline-impedance cells as the reference cell in response to a center of the one of the baseline-impedance cells corresponding to a location that is closer to a location of the catheter electrode than is any other location to which a center of any other one of the baseline-impedance cells corresponds.

23. The method according to claim 22, wherein identifying the one of the baseline-impedance cells as the reference cell comprises identifying the one of the baseline-impedance cells as the reference cell in response to the location of the catheter electrode being included in the volume to which the one of the baseline-impedance cells corresponds.

24. The method according to claim 19, wherein comparing the ascertained impedance to the baseline impedance that is specified for the reference cell comprises comparing the ascertained impedance to the baseline impedance by:
computing a ratio between a real component of the ascertained impedance and a real component of the baseline impedance, and
comparing the ratio to a ratio threshold.

25. The method according to claim 19, wherein comparing the ascertained impedance to the baseline impedance that is specified for the reference cell comprises comparing the ascertained impedance to the baseline impedance by:
computing a difference between a phase of the ascertained impedance and a phase of the baseline impedance, and
comparing the difference to a phase-difference threshold.

26. A method, comprising:
for each volume of a plurality of different volumes within a heart of a subject, ascertaining, by a processor, one or more impedances between a catheter electrode, which is in the volume, and an external electrode that is externally coupled to the subject;
constructing a baseline impedance model (BIM) that models a portion of the heart as a collection of three-dimensional cells, each of which corresponds to a respective one of the volumes, by:
for each cell of a first subset of the cells, calculating a respective representative impedance, based on the one or more impedances ascertained for the volume to which the cell corresponds, and
designating a second subset of the cells, which is a subset of the first subset of the cells, as baseline-impedance cells, each cell of which has, as a respective baseline impedance, the representative impedance of the cell;
subsequently to constructing the BIM, ascertaining that the catheter electrode is within a threshold distance of tissue of the heart, based on the baseline impedance of one of the baseline-impedance cells; and
in response to ascertaining that the catheter electrode is within the threshold distance, updating a map of the tissue.

27. The method according to claim 26, wherein calculating the representative impedance of the cell comprises calculating the representative impedance by averaging at least some of the impedances ascertained for the volume to which the cell corresponds.

28. The method according to claim 26, wherein the threshold distance is a first threshold distance, and wherein designating the second subset of the cells as the baseline-impedance cells comprises, for at least one cell of the second subset:
identifying, as a third subset of the cells, other cells of the first subset that are within a second threshold distance from the cell;
designating the cell as a potential baseline-impedance cell, based on respective representative impedances of the third subset of the cells;
subsequently to designating the cell as a potential baseline-impedance cell, identifying, as a fourth subset of the cells, other cells of the first subset that are also designated as potential baseline-impedance cells, and are within a third threshold distance from the cell; and
designating the cell as one of the baseline-impedance cells, based on respective representative impedances of the fourth subset of the cells.

29. The method according to claim 28, wherein designating the cell as a potential baseline-impedance cell comprises:
calculating at least one measure of similarity between the representative impedance of the cell and the respective representative impedances of the third subset of the cells;
calculating at least one measure of variation of the respective representative impedances of the third subset of the cells; and
designating the cell as a potential baseline-impedance cell in response to the measure of similarity and the measure of variation.

30. The method according to claim 28, wherein designating the cell as one of the baseline-impedance cells comprises:
calculating at least one measure of similarity between the representative impedance of the cell and the respective representative impedances of the fourth subset of the cells; and
designating the cell as one of the baseline-impedance cells in response to the measure of similarity.

31. The method according to claim 28, wherein designating the cell as one of the baseline-impedance cells comprises:
  fitting a line to the respective representative impedances of the fourth subset of the cells; and
  designating the cell as one of the baseline-impedance cells, in response to a distance between the representative impedance of the cell and the line being less than a fourth threshold distance.

32. The method according to claim 26, wherein the threshold distance is a first threshold distance, and wherein designating the second subset of the cells as the baseline-impedance cells comprises, for at least one cell of the second subset:
  selecting a seed cell that belongs to the second subset and is already designated as one of the baseline-impedance cells;
  identifying, as a third subset of the cells, other cells of the second subset that are already designated as respective ones of the baseline-impedance cells, and are within a second threshold distance from the seed cell;
  fitting a line to respective baseline impedances of the third subset of the cells and of the selected seed cell;
  selecting the cell, based on a distance between the cell and the seed cell being less than a third threshold distance; and
  subsequently to selecting the cell, designating the cell as one of the baseline-impedance cells, in response to a distance between the representative impedance of the cell and the line being less than a fourth threshold distance.

33. The method according to claim 32, further comprising ascertaining that a magnitude of a gradient of the line is less than a threshold gradient-magnitude value, wherein selecting the cell comprises selecting the cell in response to the magnitude of the gradient being less than the threshold gradient-magnitude value.

34. The method according to claim 26, further comprising:
  subsequently to constructing the BIM, ascertaining at least one other impedance between the catheter electrode and the external electrode; and
  reconstructing the BIM, based on the other impedance.

35. The method according to claim 34, further comprising:
  using the reconstructed BIM, ascertaining that the catheter electrode was within the threshold distance of tissue of the heart prior to the BIM having been reconstructed; and
  in response to ascertaining that the catheter electrode was within the threshold distance, updating the map of the tissue.

36. The method according to claim 26,
  wherein the catheter electrode is a first catheter electrode, the BIM is a first BIM, and the impedances are first impedances, and
  wherein the method further comprises:
    for each volume of at least some of the different volumes, ascertaining one or more second impedances between a second catheter electrode, which is in the volume, and the external electrode;
  based on the ascertained second impedances, computing a second BIM that at least partly overlaps the first BIM, each of at least some of the baseline-impedance cells of the second BIM having a baseline impedance that is different from the baseline impedance of a corresponding one of the baseline-impedance cells of the first BIM;
  ascertaining at least one scale factor that scales between the baseline impedances of the first BIM and the baseline impedances of the second BIM;
  using the ascertained scale factor, constructing a merged BIM by merging the first BIM with the second BIM;
  using the merged BIM, ascertaining that the first electrode is within the threshold distance of the tissue; and
  using the merged BIM, ascertaining that the second electrode is within the threshold distance of the tissue.

* * * * *